(12) United States Patent
Korup

(10) Patent No.: US 9,877,573 B2
(45) Date of Patent: Jan. 30, 2018

(54) DENTAL DISPENSING TIP

(71) Applicant: Young Microbrush, LLC, Grafton, WI (US)

(72) Inventor: Todd Korup, Port Washington, WI (US)

(73) Assignee: Young Microbrush, LLC, Grafton, WI (US)

( * ) Notice: Subject to any disclaimer, the term of this patent is extended or adjusted under 35 U.S.C. 154(b) by 0 days.

(21) Appl. No.: 15/239,870

(22) Filed: Aug. 18, 2016

(65) Prior Publication Data

US 2016/0353872 A1 Dec. 8, 2016

Related U.S. Application Data

(62) Division of application No. 14/193,857, filed on Feb. 28, 2014, now Pat. No. 9,427,079.

(51) Int. Cl.
*A61C 3/08* (2006.01)
*A46B 11/00* (2006.01)
(Continued)

(52) U.S. Cl.
CPC .......... *A46B 11/0006* (2013.01); *A46D 3/042* (2013.01); *A46D 9/00* (2013.01);
(Continued)

(58) Field of Classification Search
CPC ..... A61C 19/063; A61C 1/087; A61C 9/0026; A61C 5/06; A61C 5/062; A61C 5/064;
(Continued)

(56) References Cited

U.S. PATENT DOCUMENTS 1,663,439 A * 3/1928 Magnus .................. A47L 11/38
401/137
1,674,207 A * 6/1928 Krill ........................ A47L 1/08
401/15
(Continued)

FOREIGN PATENT DOCUMENTS

GB 1279839 A 6/1972
WO 9726041 A1 7/1997
(Continued)

OTHER PUBLICATIONS

International Search Report and Written Opinion dated Apr. 27, 2015 in PCT/US2015/014059.
(Continued)

*Primary Examiner* — Matthew Nelson
(74) *Attorney, Agent, or Firm* — McDermott Will & Emery LLP

(57) ABSTRACT

A dental dispensing tip includes a body having a first body end, a second body end, and a fluid passageway extending between the first and second body ends. A brush cup is provided at the second body end and has a brush barrel defined therein. A brush applicator is secured within the brush barrel and includes a plurality of bristles, wherein a first end of the brush applicator is received within the brush barrel and a second end of the brush applicator extends out of the brush barrel. A delivery cannula is in fluid communication with the fluid passageway and has a bent end entering the plurality of bristles at an intermediate location between the first and second ends to deliver the dental solution to the plurality of bristles.

15 Claims, 3 Drawing Sheets

(51) Int. Cl.
*A61C 19/06* (2006.01)
*A46D 9/00* (2006.01)
*A46D 3/04* (2006.01)
*A61C 5/62* (2017.01)

(52) U.S. Cl.
CPC .............. *A61C 5/62* (2017.02); *A61C 19/063* (2013.01); *A61C 19/066* (2013.01)

(58) Field of Classification Search
CPC ......... A61C 5/66; A61C 5/68; A46B 11/0006; A46D 3/042; A46D 9/00
USPC ................. 222/566–574; 433/80–83, 87–89; 401/129
See application file for complete search history.

(56) References Cited

U.S. PATENT DOCUMENTS

| | | | | |
|---|---|---|---|---|
| 2,582,404 | A * | 1/1952 | Zavada | A46B 11/0006 15/167.1 |
| 3,537,444 | A * | 11/1970 | Victory | A61C 17/0214 128/DIG. 10 |
| 3,547,110 | A * | 12/1970 | Balamuth | A61C 17/20 15/22.1 |
| 4,969,816 | A | 11/1990 | Drumm | |
| 4,997,371 | A | 3/1991 | Fischer | |
| 5,040,553 | A * | 8/1991 | Londono | A46B 5/02 132/311 |
| 5,087,143 | A * | 2/1992 | Hertrampf | A46B 11/0058 401/141 |
| 5,246,371 | A | 9/1993 | Fischer | |
| 5,269,684 | A | 12/1993 | Fischer | |
| 5,273,428 | A * | 12/1993 | Fischer | A61C 15/00 433/80 |
| 5,356,389 | A * | 10/1994 | Willing | A61M 25/0606 604/170.03 |
| 5,816,804 | A | 10/1998 | Fischer | |
| 6,083,002 | A * | 7/2000 | Martin | A61C 3/005 433/89 |
| 6,095,814 | A | 8/2000 | Petrich et al. | |
| 6,343,929 | B1 | 2/2002 | Fischer | |
| 6,585,512 | B2 * | 7/2003 | Van Hale | A61C 1/08 433/91 |
| 6,659,674 | B2 * | 12/2003 | Carlucci | A46B 11/06 401/282 |
| 6,805,512 | B2 * | 10/2004 | King | A45D 34/045 401/133 |
| D504,948 | S | 5/2005 | Dragan et al. | |
| 6,969,210 | B1 | 11/2005 | Newell | |
| 7,156,105 | B2 * | 1/2007 | Gueret | A45D 40/267 132/200 |
| 7,179,085 | B2 | 2/2007 | Dorsey et al. | |
| 7,198,623 | B2 | 4/2007 | Fischer et al. | |
| 7,740,479 | B2 | 6/2010 | Allred et al. | |
| 2004/0122377 | A1 | 6/2004 | Fischer | |
| 2006/0275225 | A1 * | 12/2006 | Prencipe | A46B 9/021 424/53 |
| 2007/0202459 | A1 * | 8/2007 | Boyd | A61C 17/02 433/80 |
| 2007/0262178 | A1 | 11/2007 | Fischer et al. | |
| 2010/0190132 | A1 * | 7/2010 | Taylor | |
| 2011/0123958 | A1 * | 5/2011 | Piergallini | A61C 19/063 433/217.1 |
| 2012/0077145 | A1 * | 3/2012 | Tsurukawa | A46B 5/0095 433/82 |
| 2014/0011163 | A1 * | 1/2014 | Montgomery | A61C 19/063 433/217.1 |
| 2014/0064821 | A1 * | 3/2014 | Price | A46B 11/0041 401/183 |
| 2015/0245894 | A1 | 9/2015 | Korup | |
| 2016/0324608 | A1 | 11/2016 | Frymark et al. | |

FOREIGN PATENT DOCUMENTS

| | | |
|---|---|---|
| WO | 2005037127 A1 | 4/2005 |
| WO | 2007134237 A2 | 11/2007 |

OTHER PUBLICATIONS

Supplementary European Search Report dated Jun. 22, 2017 in European Application No. 15755360.3.
Restriction Requirement dated May 1, 2015 in U.S. Appl. No. 14/193,857.
Response to Restriction Requirement filed Jun. 29, 2015 in U.S. Appl. No. 14/193,857.
Office Action dated Oct. 16, 2015 in U.S. Appl. No. 14/193,857.
Response to Office Action filed Nov. 17, 2015 in U.S. Appl. No. 14/193,857.
Office Action dated Feb. 24, 2016 in U.S. Appl. No. 14/193,857.
Response to Office Action filed Apr. 11, 2016 in U.S. Appl. No. 14/193,857.
Advisory Action dated May 2, 2016 in U.S. Appl. No. 14/193,857.
Response to Office Action filed May 17, 2016 in U.S. Appl. No. 14/193,857.
Notice of Allowance dated Jul. 6, 2016 in U.S. Appl. No. 14/193,857.
Office Action dated Dec. 29, 2016 in Design U.S. Appl. No. 29/548,917.
Response to Office Action filed Feb. 16, 2017 in Design U.S. Appl. No. 29/548,917.
Notice of Allowance dated Mar. 7, 2017 in Design U.S. Appl. No. 29/548,917.

* cited by examiner

DENTAL DISPENSING TIP

This application is a divisional of and claims priority to U.S. patent application Ser. No. 14/193,857, which was filed on Feb. 28, 2014.

BACKGROUND

The present disclosure relates to tools used in the field of dentistry and, more particularly, to dental dispensing tips used to deliver dental solutions to a tooth surface.

In the field of dentistry, various dental medicaments and solutions are applied to the teeth of a patient as part of routine dental cleaning, preparation, and restorative processes. During dental cleaning processes, for example, fluoride is often applied to teeth to prevent tooth decay, wherein the fluoride hardens the enamel tooth surface by forming calcium fluoride. One method of applying fluoride to teeth is by dispensing a fluoride gel composition into a dental tray and subsequently placing the dental tray over the teeth of the patient. The tray holds the fluoride gel composition adjacent to the teeth and, after a desired amount of time, the dental tray is removed and the remaining fluoride gel composition is then rinsed off the teeth.

Another method involves the direct application of a fluoride varnish to the teeth of a patient. Fluoride varnish typically includes a mixture of fluoride salt dispersed within a sticky, adhesive hydrophobic varnish material. The fluoride varnish is usually stored within a dedicated cup or tray that can be accessed by the dental practitioner. The dental practitioner dips a brushed dental applicator or "dental brush" into the cup or tray and brushes the fluoride varnish onto the teeth. Once applied, the fluoride varnish adheres to the teeth and subsequently erodes away after several hours.

Today, there are various dental dispensing tips having brush applicators that can be used to deliver dental solutions to the teeth of a patient. For example, combination applicator and syringe dental dispensing tips often include an associated brush applicator disposed on its distal end. However, current dental dispensing tips are unable to adequately dispense high-viscosity liquid dental solutions due to the resulting high capillary action of the dental solutions. More specifically, the bristles of conventional brush applicators are usually formed through known flocking methods, such as electrostatic flocking or gravity flocking. Flocked brush applicators, however, tend to introduce bubbles into high-viscosity dental solutions as the dental solution is expressed through the bristles. Alternatively, other methods of manufacturing the brush applicators do not allow an adequate amount of brush bristles to be available to spread the dental solution and are therefore ineffective.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure relates to tools used in the field of dentistry and, more particularly, to dental dispensing tips used to deliver dental solutions to a tooth surface.

The embodiments disclosed herein provide an efficient method of applying a dental solution to the teeth of a patient. As described herein, dental solutions that are typically sold in individual dosages, such as fluoride varnishes or other flowable dental composites, can be used with the presently disclosed dental dispensing tips, and thereby saving the dental practitioner valuable application time. The exemplary dental dispensing tips described herein below provide a brush applicator including a plurality of bristles that may be secured in the dental dispensing tip, such as through a tufting process or the like. In some cases, the dental solution is conveyed directly into the bristles of the brush applicator with a delivery cannula extending from a fluid passageway in fluid communication with the source of the dental solution. The delivery cannula may be configured to deliver the dental solution to an intermediate portion of the brush applicator, where the bundled bristles are less dense and therefore more amenable to the introduction of the dental solution. The manufacturing techniques described herein allow the dental dispensing tips to be disposable and cost-effective.

Figure 1A:
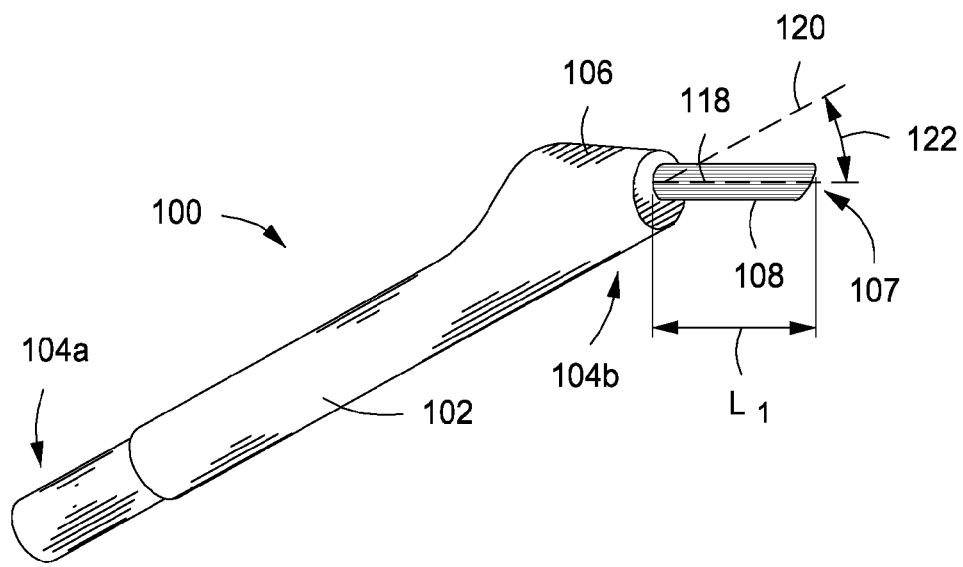
FIG. 1A illustrates an isometric view of an exemplary dental dispensing tip, according to one or more embodiments.
Figure 1B:
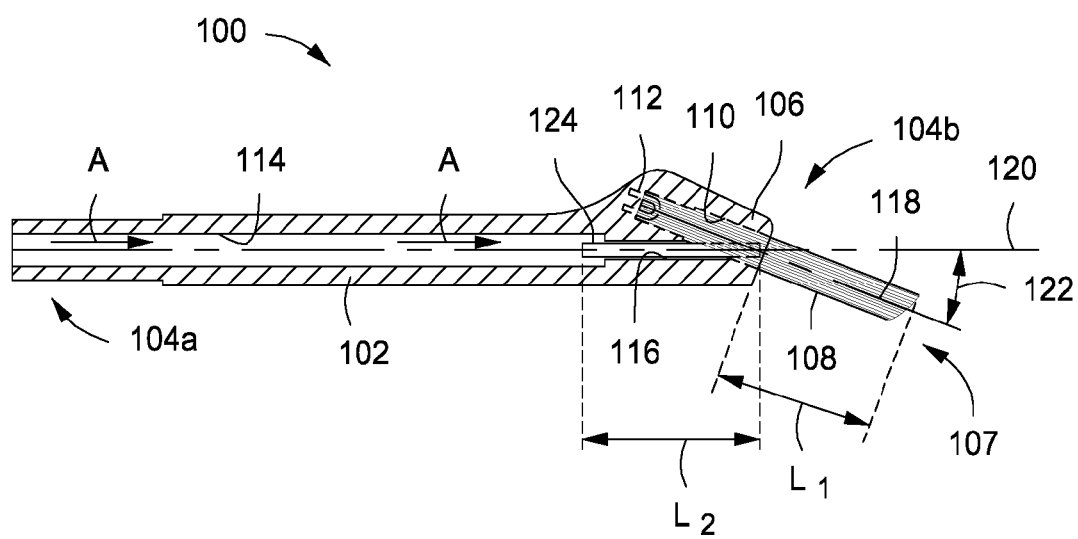
FIG. 1B illustrates a cross-sectional view of the exemplary dental dispensing tip of FIG. 1A, according to one or more embodiments.

Referring to FIGS. 1A and 1B, illustrated are isometric and cross-sectional views, respectively, of an exemplary dental dispensing tip 100, according to one or more embodiments of the present disclosure. As discussed herein, the dental dispensing tip 100 (hereafter "the tip 100") may be particularly useful in dispensing dental solutions that exhibit relatively high viscosities. For example, the tip 100 may be configured to suitably dispense dental solutions that exhibit a viscosity of at least 700 centipoise and otherwise exhibit a viscosity that ranges between about 700 centipoise and about 10,000 centipoise.

Dental solutions that may be delivered using the tip 100 may be any flowable dental composite, or any type of gel or paste that is commonly applied to teeth during dental cleaning, preparation, and restorative processes. Exemplary dental solutions that may be used in conjunction with the tip 100 include, but are not limited to, fluoride varnish, flowable composites, whitening solutions and gels, cements, bonding agents, desensitizers, and etchants.

As illustrated, the tip 100 may include a generally elongate body 102 having a first or proximal end 104a and a second or distal end 104b. The body 102 may be made of plastic, such as polypropylene, but could equally be made of any other rigid material (e.g., a metal, a composite material, etc.), without departing from the scope of the disclosure. In some embodiments, the first end 104a may provide a location for the tip 100 to be fluidly and operatively coupled to a dental solution source (not shown) configured to provide the dental solution to the tip 100 for application. Exemplary dental solution sources may include Luer lock syringes, sealed ampoules, or other types of unit dose packaging configurations used for delivering dental solutions. In some embodiments, the first end 104a may be threaded to accommodate corresponding Luer-Lok connection fittings. In other embodiments, the first end 104a may be configured to allow an ampoule to form a snap-fit or threaded connection to the tip 100. In yet other embodiments, the dental solution source and the tip 100 may be integrally formed, without departing from the scope of the disclosure.

The second end 104b may generally provide a head or brush cup 106 configured to receive or otherwise house a brush applicator 107 therein. As described below, the brush applicator 107 may be used to apply the dental solution directly to the teeth of a patient. As illustrated, the brush applicator 107 may include a plurality of bristles 108, and the brush cup 106 may define a central orifice or brush barrel 110 configured to receive and secure the bristles 108 therein for operation. In some embodiments, the brush applicator 107 may be secured within the brush barrel 110 via a tufting process configured to fasten the brush applicator 107 within the brush cup 106. In an exemplary tufting process, the plurality of bristles 108 are gathered together in a bundle and bent in half using a mechanical fastener 112 (FIG. 1B), such as a staple or another type of rigid wire. Once bent in half, the mechanical fastener 112 is wrapped at least partially around the bundle of bristles 108 at the proximal end of the brush applicator 107, and the ends of the bristles 108 are generally aligned at the distal end of the brush applicator 107.

A driver mechanism (not shown) may then be actuated to force the brush applicator 107 into the brush barrel 110 such that the mechanical fastener 112 is driven toward the bottom of the brush barrel 110 and the ends of the bristles 108 remain partially extended out of the brush barrel 110. In some cases, an interference fit is generated between the inner wall of the brush barrel 110 and the bundle of bristles 108 and thereby prevents removal of the brush applicator 107. In other cases, however, the driver mechanism may be configured to embed and otherwise drive the mechanical fastener 112 into the bottom of the brush barrel 110, thereby mechanically fastening the brush applicator 107 in place within the brush barrel 110.

In other embodiments, the brush applicator 107 may be secured within the brush barrel 110 using solely an interference fit. More particularly, a bundle of the bristles 108 (not necessarily bent in half as in the tufting process) may be forced under pressure axially into the brush barrel 110 and generally prevented from removal therefrom as a result of the friction generated between the inner wall of the brush barrel 110 and the bristles 108. As illustrated, the brush barrel 110 may define more than one diameter along its axial length, or may alternatively provide a tapered diameter. As will be appreciated, the variable diameter of the brush barrel 110 may prove advantageous in helping to facilitate an interference fit. In yet other embodiments, however, the brush applicator 107 may be secured within the brush barrel 110 using an adhesive or an epoxy. As will be appreciated, any combination of the preceding methods of securing the brush applicator 107 in the brush barrel 110 may be used, without departing from the scope of the disclosure.

The bristles 108 may be made of or otherwise constitute reasonably soft fibers or filaments so as not to irritate target dental surfaces. Both natural and synthetic fibers or filaments may be used to form the bristles 108. Suitable natural fibers include, but are not limited to, cotton fibers, celluloses, gums, carbopolymers, water-dispersible polymers, and any combination thereof. Suitable synthetic fibers can include, but are not limited to, nylon, polyesters, polyamides, polyolefins, polypropylenes, polyvinylpyrrolidone, and any combination thereof. In at least one embodiment, the bristles 108 may be made of extruded nylon fibers, such as TYNEX® nylon filaments commercially available through E. I. du Pont de Nemours and Company. In addition, various injection moldable plastics may be formed as the bristles 108 using standard injection molding techniques, without departing from the scope of the disclosure.

The brush applicator 107 may include any number of fibers or filaments that make up the bundle of bristles 108 that extends out of the brush barrel 110. In some embodiments, for example, the brush applicator 107 may include or otherwise encompass about 200 individual bristle 108 strands that are folded in half during the tufting process described above. As a result, about 400 ends of the bristles 108 may extend out of the brush cup 106 to contact the teeth surfaces during application of the dental solution. The diameter of each individual bristle 108 may vary depending on the application and the material used to make the bristles 108. In some embodiments, for example, the diameter of each bristle 108 may range between about 0.02 mm and about 0.3 mm. In other embodiments, the diameter of each bristle 108 may range between about 0.06 mm and about 0.09 mm. As will be appreciated by those skilled in the art, the actual selected range of fiber diameter for the bristles 108 may depend on the viscosity, surface tension, cohesiveness, and other physical properties of the dental solution to be delivered through the tip 100.

The brush applicator 107 may be configured and otherwise coupled to the brush cup 106 such that a portion of the bristles 108 extends out of the brush barrel 110 to a predetermined distance or length $L_1$. As with the diameter of each bristle 108, the actual selected length $L_1$ that the bristles 108 are to extend out of the brush barrel 110 may depend on the viscosity, surface tension, cohesiveness, and other physical properties of the dental solution to be delivered through the tip 100. In at least one embodiment, the length $L_1$ may range between about 0.125 inches and about 0.75 inches. As will be appreciated, however, other ranges for the length $L_1$ that are less than 0.125 inches and greater than 0.75 inches are also contemplated herein, without departing from the scope of the disclosure.

Referring specifically to FIG. 1B, the tip 100 may further include a fluid passageway 114 and a delivery orifice 116 defined within the body 102. As illustrated, the fluid passageway 114 may extend from the first end 104a toward the second end 104b, and the delivery orifice 116 may extend from the fluid passageway 114 to the brush barrel 110. As a result, the delivery orifice 116 may be configured to place the fluid passageway 114 in direct fluid communication with the brush barrel 110. Accordingly, the fluid passageway 114 and the delivery orifice 116 may be configured to cooperatively convey the dental solution from a dental solution source (not shown) coupled to the first end 104a of the tip 100 to the brush cup 106.

In some embodiments, as illustrated, the delivery orifice 116 may have a diameter that is smaller than the diameter of the fluid passageway 114. In other embodiments, however, the fluid passageway 114 and the delivery orifice 116 may exhibit the same diameter and may otherwise be characterized as a single, continuous fluid conduit that feeds the dental solution directly to the brush barrel 110. In the illustrated embodiment, the smaller internal diameter of the delivery orifice 116 may prove advantageous in restricting, but not completely precluding, fluid flow therethrough. For example, a dental solution that exhibits a viscosity of at least 1000 centipoise will not readily flow through the delivery orifice 116 absent an applied hydraulic pressure, such as hydraulic pressure applied by a dental practitioner. As will be appreciated, this feature may prevent the dental solution from running or dripping out of the tip 100, and thereby resulting in a mess or dripping into the mouth of the patient, which could be particularly disadvantageous if the dental solution has an undesirable taste.

As illustrated, the brush cup 106 may be angularly-offset from the body 102. More particularly, the brush cup 106 may have a central axis 118 that is offset from a central axis 120 of the body 102 by a predetermined angle 122. The angle 122 of offset between the brush cup 106 and the body 102 may range between about 15° to about 45°. In at least one embodiment, the angle 122 of offset between the brush cup 106 and the body 102 may be about 22.5°.

As will be appreciated, the angled configuration of the brush cup 106 with respect to the body 102 may prove advantageous in allowing the dental solution to more easily enter the brush applicator 107 for delivering the dental solution to surfaces of teeth. More particularly, is it difficult to express fluids (i.e., the dental solution) through tightly packed bristles 108, such as would be found at the bottom of the bristles 108 (i.e., the tufted end) where the mechanical fastener 112 tightly packs and couples the bristles 108 to the brush cup 106. Having the brush cup 106 extend at the angle 122 may allow any fluids delivered to the brush barrel 110 via the delivery orifice 116 to bypass the tufted end of the brush applicator 107 and instead be injected at an intermediate location between the tufted and exposed ends of the bristles 108. As can be appreciated, the intermediate location in the bristles 108 may be less dense than the tufted end, thereby being more amenable to the introduction of the fluid therethrough.

In some embodiments, the tip 100 may further include a delivery cannula 124 configured to be arranged within the delivery orifice 116. During manufacturing of the tip 100, the delivery cannula 124 may be inserted or otherwise installed into the delivery orifice 116 via either the first end 104a or the second end 104b. In some embodiments, the delivery cannula 124 may be secured within the delivery orifice 116 using an interference fit between the outer radial surface of the delivery cannula 124 and the inner wall of the delivery orifice 116. In other embodiments, the delivery cannula 124 may be secured within the delivery orifice 116 using an adhesive or epoxy, or through sonic welding techniques, without departing from the scope of the disclosure. In any event, the delivery cannula 124 may be secured within the delivery orifice 116 such that it is able to withstand the hydraulic pressures involved in conveying a dental solution through the delivery orifice 116 and into the brush cup 106.

The delivery cannula 124 may be made of any rigid material including, but not limited to, plastics, metals, ceramics, composite materials, or any combination thereof. The diameter or size of the delivery cannula 124 may vary, depending primarily on the configuration of the tip 100 (e.g., the size of the delivery orifice 116) and the type of dental solution being applied with the brush applicator 107. For instance, a larger size cannula 124 may be preferred and employed in order to convey higher viscosity dental solutions. A larger cannula 124 may also allow a dental solution to be applied at an increased flow rate. As will be appreciated, the delivery cannula 124 may be designed and otherwise manufactured to meet any desired size and application constraints. Exemplary sizes for the delivery cannula 124 may range from about 15 gauge to about 25 gauge. In at least one embodiment, the size of the delivery cannula 124 may range between about 18 gauge to about 20 gauge.

As illustrated, the delivery cannula 124 may exhibit a length $L_2$ that is sufficient to introduce or otherwise extend one end (e.g., the distal end) of the delivery cannula 124 at least partially into the bristles 108. As will be appreciated, having an end of the delivery cannula 124 at least partially extended into the bristles 108 may prove advantageous in more efficiently delivering and otherwise expressing the dental solution into portions of the bristles 108 that are less dense. The length $L_2$ may be limited, however, in order to ensure that the delivery cannula 124 does not extend to a point where it may inadvertently contact and damage the teeth of a patient and otherwise obstruct the dental solution application on the teeth. In some embodiments, the length $L_2$ may also be sufficient to extend the opposing end (e.g., the proximal end) of the delivery cannula 124 a short distance into the fluid passageway 114, as illustrated.

In exemplary operation, a dental solution may be introduced into the fluid passageway 114, as indicated by the arrows A. As discussed above, the dental solution A may be derived from a dental solution source (not shown) fluidly coupled to the first end 104a of the tip 100 or otherwise configured to deliver the dental solution into the fluid passageway 114. In some embodiments, the dental solution A may be hydraulically forced through the fluid passageway 114 and the delivery orifice 116, until subsequently being injected into the brush barrel 110. Once in the brush barrel 110, the dental solution A may be expressed into the bristles 108 of the brush applicator 107. Advantageously, the tip 100 is configured and otherwise designed such that the dental solution A is introduced into the brush applicator 107 at the intermediate location between the tufted and exposed ends of the bristles 108. At the intermediate location, the bristles 108 are less dense and therefore more amenable to receiving the dental solution A within the fibrous bundle. In some embodiments, as described above, the delivery cannula 124 may be used to deliver the dental solution A directly into the interior of the bristles 108 of the brush applicator 107. The dental solution A may then flow toward the distal end of the brush applicator 107 and a dental practitioner may then be able to apply the dental solution A to the teeth of a patient as desired.

Figures 2A, 2B:
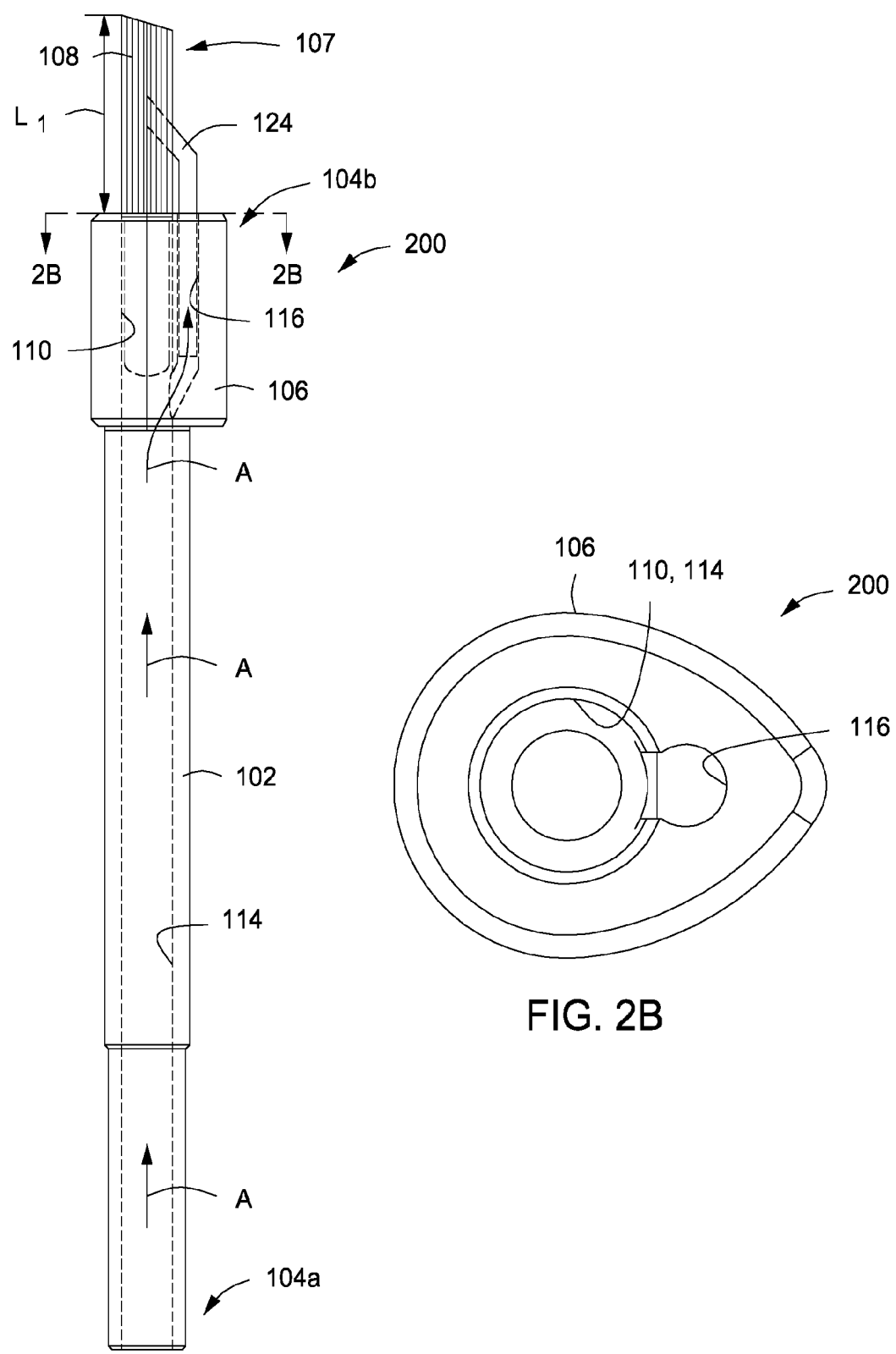
FIG. 2A illustrates a side view of another exemplary dental dispensing tip, according to one or more embodiments.
FIG. 2B illustrates a top view of the exemplary dental dispensing tip of FIG. 2A, according to one or more embodiments.

Referring now to FIGS. 2A and 2B, with continued reference to FIGS. 1A and 1B, illustrated are side and top views, respectively, of another exemplary dental dispensing tip 200, according to one or more embodiments. The dental dispensing tip 200 (hereafter "the tip 200") may be similar in some respects to the tip 100 of FIGS. 1A and 1B and therefore may be best understood with reference thereto, where like numerals represent like elements not described again in detail. As with the tip 100, the tip 200 may be particularly useful in dispensing dental solutions that exhibit relatively high viscosities. The tip 200 may include the body 102 having the first and second ends 104a,b and the brush cup 106 may be arranged or otherwise disposed at the second end 104b.

The brush applicator 107, including the plurality of bristles 108, may be disposed and secured within the brush barrel 110 of the brush cup 106. As generally described above, the brush applicator 107 may be secured within the brush barrel 110 via several different processes, without departing from the scope of the disclosure. In some embodiments, for instance, the brush applicator 107 may be secured within the brush barrel 110 via a tufting process that mechanically fastens the brush applicator 107 within the brush cup 106 and/or generates an interference fit between the brush barrel 110 and the bristles 108, thereby preventing removal of the brush applicator 107. In other embodiments, the brush applicator 107 may be secured within the brush barrel 110 using solely an interference fit or with the use of an adhesive or an epoxy. As illustrated, the bristles 108 extend out of the brush barrel 110 to the distance or length $L_1$.

As shown in FIG. 2A, the tip 200 may further include the fluid passageway 114 (shown in dashed) and the delivery orifice 116 (shown in dashed) defined within the interior of the body 102. In the tip 200 of FIGS. 2A and 2B, however, the fluid passageway 114 may be configured to extend the entire axial distance between the first and second ends end 104a,b and otherwise fluidly communicate with the brush barrel 110. In other words, the brush barrel 110 may form an integral part or extension of the fluid passageway 114.

The delivery orifice 116 may extend laterally from the fluid passageway 114 and through a portion of the brush cup 106 before eventually exiting the brush cup 106 at the second end 104b of the tip 200. In some embodiments, as illustrated, the delivery orifice 116 may have a diameter that is smaller than the diameter of the fluid passageway 114. As best seen in the top view of FIG. 2B, where the brush applicator 107 is removed for ease of viewing, the delivery orifice 116 may exit the brush cup 106 in a location that is laterally-offset from the brush barrel 110 (i.e., the fluid passageway 114). To accommodate the location of the delivery orifice 116, the brush cup 106 may be in the general shape of an oval or otherwise elliptical. In other embodiments, however, the brush cup 106 may be large enough such that a substantially circular shape may be used, without departing from the scope of the disclosure.

With the brush applicator 107 secured within the brush barrel 110 (i.e., the fluid passageway 114), a generally sealed interface may be formed within the fluid passageway 114 with the tightly-packed bristles 108. As a result, little or no dental solution may be able to traverse the proximal end (i.e., the tufted end) of the brush applicator 107 within the fluid passageway 114. Instead, the delivery orifice 116 may be used to convey the dental solution to the bristles 108 of the brush applicator 107. More specifically, the tip 200 may further include the delivery cannula 124 configured to be arranged at least partially within the delivery orifice 116. During manufacturing of the tip 200, the delivery cannula 124 may be secured within the delivery orifice 116 before, during, or after installation of the brush applicator 107. As with the tip 100 of FIGS. 1A-1B, the delivery cannula 124 of the tip 200 may be secured within the delivery orifice 116 using an interference fit, an adhesive or epoxy, or through sonic welding techniques. Once secured within the delivery orifice 116, the delivery cannula 124 may be able to withstand the hydraulic pressures involved in conveying a dental solution through the delivery orifice 116.

As illustrated, an upper end 202 of the delivery cannula 124 may be configured to extend out of the delivery orifice 116 and into the brush applicator 107. More particularly, following installation of the brush applicator 107 within the brush cup 106, the upper end 202 may be bent or otherwise directed into the bristles 108 at an intermediate location between the tufted and exposed ends of the brush applicator 107. As a result, the delivery cannula 124 may provide a direct fluid conduit into the bristles 108 from the fluid passageway 114 and the delivery conduit 116. Since it is difficult to express fluids through the tightly packed bristles 108 at the tufted end of the brush applicator 107, having the upper end 202 of the delivery cannula 124 extended into the bristles 108 may help deliver the dental solution into portions of the bristles 108 that are less dense.

In exemplary operation, a dental solution may be introduced into the fluid passageway 114, as indicated by the arrows A. The dental solution A may be hydraulically forced through the fluid passageway 114 to the delivery orifice 116 and into the delivery cannula 124. Continued application of hydraulic pressure may convey the dental solution A into the bristles 108 of the brush applicator 107 via the upper portion 202 of the delivery cannula 124 that is bent into the bundle of bristles 108. Advantageously, the dental solution A is introduced into the bristles 108 at the intermediate location between the tufted and exposed ends of the brush applicator 107 and otherwise where the bristles 108 are less dense and therefore more amenable to receiving the dental solution A. The dental solution A may then flow toward the distal end of the brush applicator 107 and a dental practitioner may then be able to apply the dental solution A to the teeth of a patient as desired.

Figure 3:
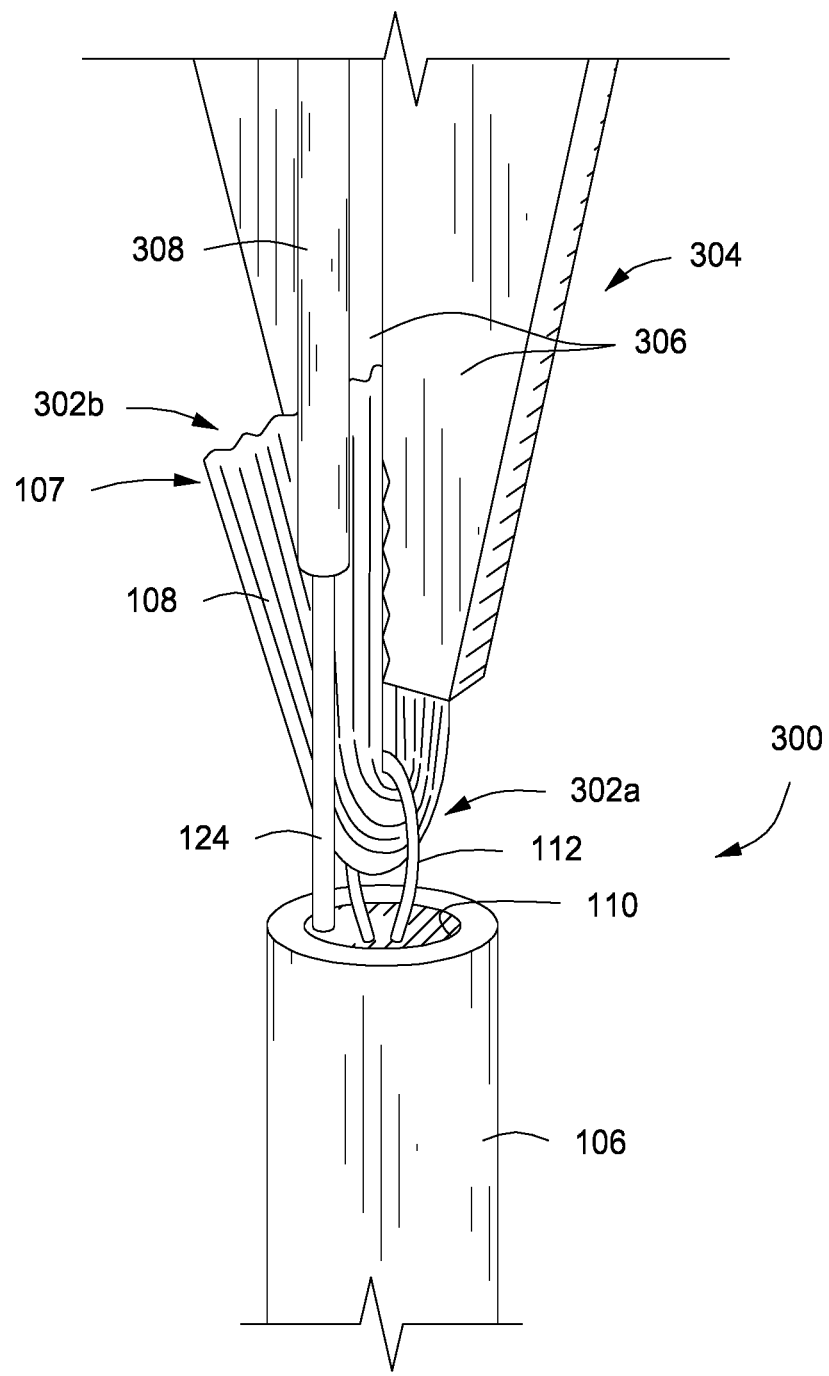
FIG. 3 illustrates another exemplary dental dispensing tip, according to one or more embodiments.

Referring now to FIG. 3, with continued reference to the prior figures, illustrated is another exemplary dental dispensing tip 300, according to one or more embodiments. More particularly, FIG. 3 illustrates only a portion of the dental dispensing tip 300 (hereafter "the tip 300") and otherwise illustratively depicts an exemplary method of assembling or manufacturing the tip 300. The tip 300 may be similar in some respects to the tips 100 and 200 of FIGS. 1A-1B and 2A-2B, respectively, and therefore may be best understood with reference thereto, where like numerals will again represent like elements not described again.

As illustrated in FIG. 3, the tip 300 may include the brush cup 106 and the brush applicator 107, including the plurality of bristles 108. The brush applicator 107 may be configured to be disposed and otherwise secured within the brush barrel 110 defined in the brush cup 106. In the illustrated embodiment, the brush applicator 107 is shown in the process of being secured within the brush barrel 110 via a tufting process. The delivery cannula 124 may also be included in the tip 300 and configured to be installed within the brush cup 106 simultaneously with the brush applicator 107.

In the depicted tufting process, the plurality of bristles 108 may be gathered together in a bundle and bent in half using the mechanical fastener 112. Once bent in half, the mechanical fastener 112 is at least partially wrapped around the bundle of bristles 108 at a proximal end 302a of the brush applicator 107, and the ends of the bristles 108 are generally arranged and aligned at a distal end 302b of the brush applicator 107. A driver mechanism 304 associated with a tufting machine (not shown) may then be actuated to force the brush applicator 107 into the brush barrel 110 such that the mechanical fastener 112 is driven toward the bottom of the brush barrel 110. As illustrated, the driver mechanism 304 may include jaws 306 configured to engage the mechanical fastener 112 and thrust the brush applicator 107 into the brush cup 106.

In some embodiments, an interference fit is generated between the inner wall of the brush barrel 110 and the bundle of bristles 108 and the brush applicator 107 is thereby prevented from removal. In other embodiments, however, the driver mechanism 304 may be configured to embed and otherwise drive the mechanical fastener 112 into the bottom of the brush barrel 110, thereby mechanically fastening the brush applicator 107 in place within the brush barrel 110.

In at least one embodiment, the driver mechanism 304 may further include a secondary driver 308 configured to install the delivery cannula 124 into the brush cup 106 simultaneously with the brush applicator 107. More particularly, the secondary driver 308 may be configured to grip or otherwise engage an end of the delivery cannula 124 and descend toward the brush cup 106 concomitantly with the jaws 306, thereby securing the delivery cannula 124 within the brush barrel 110 via an interference fit. After properly placing the delivery cannula 124 within the brush cup 106, the secondary drive 308 may then release its grip or otherwise disengage the delivery cannula 124. Similar to the delivery cannula 124 of the tip 200 of FIGS. 2A-2B, the distal end of the delivery cannula 124 may subsequently be bent or otherwise directed into the bristles 108 at an intermediate location between the distal and proximal ends 302*a*,*b* of the brush applicator 107. As a result, a direct fluid conduit into the bristles 108 from the fluid passageway 114 (not shown) may be generated via the delivery cannula 124.

With the brush applicator 107 secured within the brush barrel 110, a generally sealed interface may be formed with the tightly-packed bristles 108 such that little or no dental solution may be able to traverse the proximal end (i.e., the tufted end) of the brush applicator 107. Rather, the delivery cannula 124 may be used to convey the dental solution to the bristles 108 of the brush applicator 107. In exemplary operation, the dental solution may be introduced into the fluid passageway 114 (not shown) and directed through the delivery cannula 124 in order to bypass the proximal end (i.e., the tufted end) of the brush applicator 107. Continued application of hydraulic pressure may force the dental solution A into the bristles 108 of the brush applicator 107 via the bent portion of the delivery cannula 124. Again, the dental solution A is advantageously introduced into the bristles 108 at an intermediate location between the tufted and exposed ends of the brush applicator 107 and otherwise where the bristles 108 are less dense and therefore more amenable to receiving the dental solution A. The dental solution A may then flow toward the distal end of the brush applicator 107 and a dental practitioner may then be able to apply the dental solution A to the teeth of a patient as desired.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A dental dispensing tip, comprising:
   a body having a first body end, a second body end, and a fluid passageway extending between the first and second body ends, the fluid passageway being configured to receive a dental solution therein;
   a brush cup provided at the second body end and having a brush barrel defined therein;
   a brush applicator secured within the brush barrel and including a plurality of bristles, wherein a first end of the brush applicator is received within the brush barrel and a second end of the brush applicator extends out of the brush barrel; and
   a delivery cannula in fluid communication with the fluid passageway and having a bent end entering the plurality of bristles at an intermediate location between the first and second ends to deliver the dental solution to the plurality of bristles.

2. The dental dispensing tip of claim 1, wherein the first body end is configured to be coupled to a dental solution source that provides the dental solution to the fluid passageway.

3. The dental dispensing tip of claim 1, wherein the brush applicator is secured within the brush barrel using at least one of a tufting process, an interference fit, and an adhesive or an epoxy.

4. The dental dispensing tip of claim 1, further comprising a delivery orifice defined in the body and extending from the fluid passageway, the delivery orifice being configured to receive the delivery cannula therein.

5. The dental dispensing tip of claim 4, wherein the delivery orifice extends parallel to and laterally offset from the fluid passageway and exits the brush cup at the second body end.

6. The dental dispensing tip of claim 1, wherein the brush barrel forms an extension of the fluid passageway.

7. The dental dispensing tip of claim 1, wherein the body and the brush cup are integrally formed as a monolithic structure.

8. The dental dispensing tip of claim 1, wherein the plurality of bristles are secured within the brush cup with a mechanical fastener embedded into a base of the brush barrel.

9. The dental dispensing tip of claim 8, wherein the mechanical fastener bends the plurality of bristles in half and thereby provides a tufted end of the plurality of bristles that is secured within the brush cup.

10. The dental dispensing tip of claim 1, wherein the plurality of bristles are secured within the brush barrel with an interference fit.

11. The dental dispensing tip of claim 1, wherein the plurality of bristles is made from a material selected from the group consisting of cotton fibers, celluloses, gums, carbopolymers, water-dispersible polymers, nylon, polyesters, polyamides, polyolefins, polypropylenes, polyvinylpyrrolidone, injection moldable plastics, and any combination thereof.

12. A method, comprising:
  introducing a dental solution into a dental dispensing tip that includes:
    a body having a first body end, a second body end, and a fluid passageway extending between the first and second body ends;
    a brush cup provided at the second body end and having a brush barrel defined therein;
    a brush applicator secured within the brush barrel and including a plurality of bristles, wherein a first end of the brush applicator is received within the brush barrel and a second end of the brush applicator extends out of the brush barrel; and
    a delivery cannula in fluid communication with the fluid passageway and having a bent end entering the plurality of bristles at an intermediate location between the first and second ends;
  conveying the dental solution from the fluid passageway into the delivery cannula;
  expressing the dental solution into the plurality of bristles at the intermediate location via the bent end of the delivery cannula; and
  applying the dental solution to a tooth of a patient with the brush applicator.

13. The method of claim 12, further comprising conveying the dental solution into the fluid passageway from a dental solution source coupled to the first end of the dental dispensing tip.

14. The method of claim 12, wherein the dental dispensing tip further includes a delivery orifice defined in the body and extending from the fluid passageway, the delivery cannula being arranged within the delivery orifice, and wherein conveying the dental solution to the delivery cannula comprises:
  conveying the dental solution to the delivery orifice from the fluid passageway; and
  delivering the dental solution to the delivery cannula from the delivery orifice.

15. The method of claim 12, wherein the brush barrel forms an extension of the fluid passageway, the method further comprising sealing the fluid passageway at the brush barrel with the first end of the brush applicator.

* * * * *